United States Patent [19]
Beihoffer et al.

[11] Patent Number: 5,962,578
[45] Date of Patent: Oct. 5, 1999

[54] POLY(DIALKYLAMINOALKYL (METH)ACRYLAMIDE)-BASED SUPERABSORBENT GELS

[75] Inventors: Thomas W. Beihoffer, Arlington Heights; Michael A. Mitchell, Lake Zurich; Leticia L. Trzupek, Hoffman Estates, all of Ill.

[73] Assignee: AMCOL International Corporation

[21] Appl. No.: 08/974,118

[22] Filed: Nov. 19, 1997

[51] Int. Cl.[6] .............................. C08F 39/00; C08F 33/00
[52] U.S. Cl. ..................... 524/521; 524/501; 524/555; 524/556; 524/922; 525/217; 525/218; 525/328.2; 525/359.5
[58] Field of Search ..................... 524/555, 556, 524/501, 521, 922; 525/217, 218, 328.2, 359.5

[56] References Cited

U.S. PATENT DOCUMENTS

| | | | |
|---|---|---|---|
| 4,018,826 | 4/1977 | Gless, Jr. et al. | 260/583 P |
| 4,237,067 | 12/1980 | Küster et al. | 564/205 |
| 4,818,598 | 4/1989 | Wong | 428/284 |
| 5,085,787 | 2/1992 | Pinschmidt, Jr. et al. | 252/8.551 |
| 5,274,018 | 12/1993 | Tanaka et al. | 524/166 |
| 5,340,865 | 8/1994 | Neff et al. | 524/922 |
| 5,384,343 | 1/1995 | Farrar et al. | 524/556 |
| 5,669,894 | 9/1997 | Goldman et al. | 604/368 |
| 5,681,889 | 10/1997 | Kondo et al. | 525/218 |
| 5,763,523 | 6/1998 | Chen et al. | 524/922 |
| 5,763,530 | 6/1998 | Chen et al. | 524/521 |
| 5,849,862 | 12/1998 | Davies et al. | 524/555 |

FOREIGN PATENT DOCUMENTS

| | | | |
|---|---|---|---|
| WO 96/15163 | 5/1996 | WIPO | C08F 20/56 |
| WO 96/15180 | 5/1996 | WIPO | C08J 5/02 |
| WO 96/17681 | 6/1996 | WIPO | B01J 20/00 |
| WO 98/24832 | 6/1998 | WIPO | C08J 3/075 |
| WO 98/37149 | 8/1998 | WIPO | C08L 101/14 |

OTHER PUBLICATIONS

Chang et al., "Water–soluble copolymers. 49. Effect of the distribution of the hydrophobic cationic monomer dimethyldodecyl(2–acrylamidoethyl)ammonium bromide on the solution behavior of associating acrylamide copolymers," *Macromolecules*, 26, pp. 6121–6126 (1993).

*Primary Examiner*—Andrew E. C. Merriam
*Attorney, Agent, or Firm*—Marshall, O'Toole, Gerstein, Murray & Borun

[57] ABSTRACT

Poly(dialkylaminoalkyl (meth)acrylamide)-based superabsorbent gels are disclosed. The superabsorbent gels either comprise a mixture of a poly(dialkylaminoalkyl (meth)acrylamide) polymer and an acidic water-absorbing polymer, like polyacrylic acid, or comprise a salt of a poly(dialkylaminoalkyl (meth)acrylamide) polymer. An improved method of preparing an N-(dialkylaminoalkyl)(meth)acrylamide monomer also is disclosed.

19 Claims, 6 Drawing Sheets

POLY(DIALKYLAMINOALKYL (METH) ACRYLAMIDE)-BASED SUPERABSORBENT GELS

FIELD OF THE INVENTION

The present invention relates to superabsorbent gels containing a poly(dialkylaminoalkyl (meth)acrylamide), or a salt thereof, and to an improved method of manufacturing an N-(dialkylaminoalkyl) (meth)acrylamide monomer. The superabsorbent gels comprise a poly(dialkylaminoalkyl (meth)acrylamide), and preferably a poly(dialkylaminoalkyl (meth)acrylamide) admixed with an acidic superabsorbent polymer, like a polyacrylic acid, or comprise a salt of a poly(dialkylaminoalkyl (meth)acrylamide).

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. No. 5,669,894. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP in a hygienic article, like a diaper.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers do not function as effective SAPs in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, like urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, like urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

Prior investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, like polyacrylic acid, and an amount of an ionizable surfactant sufficient to form at least a monolayer of surfactant on the polymer. In another embodiment, a cationic gel, like a gel containing quaternized ammonium groups and in the hydroxide (i.e., OH) form, is used with an anionic gel (i.e., a polyacrylic acid) to remove electrolytes from the solution by ion exchange.

Wong U.S. Pat. No. 4,818,598 discloses the addition of a fibrous anion exchange material, like DEAE cellulose, to a hydrogel, like a polyacrylate, to improve absorption properties. WO 96/17681 discloses combining an anionic SAP, like polyacrylic acid, with a polysaccharide-based cationic SAP to overcome the salt poisoning effect. Similarly, WO 96/15163 discloses combining a cationic SAP having at least 20% of the functional groups in a basic (i.e., OH) form with a cationic exchanges resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect. It would be desirable, however, to provide an SAP that exhibits exceptional absorption and retention, like a sodium polyacrylate, and, therefore, can be used alone as an SAP. It also would be desirable to admix such an SAP with polyacrylic acid, or another acid-containing SAP, to overcome the salt poisoning effect.

SUMMARY OF THE INVENTION

The present invention is directed to poly (dialkylaminoalkyl acrylamide)-based superabsorbent gels and poly(dialkylaminoalkyl methacrylamide)-based superabsorbent gels, hereafter collectively referred to as poly (dialkylaminoalkyl (meth)acrylamides). A poly (dialkylaminoalkyl (meth)acrylamide) polymer can be used in conjunction with an acidic water-absorbing resin, like polyacrylic acid, to help overcome the salt poisoning effect, or a salt of a poly(dialkylaminoalkyl (meth)acrylamide) polymer can be used alone as an SAP. The poly (dialkylaminoalkyl (meth)acrylamide) polymer also can be used, alone, as an SAP to absorb and retain acidic media. More particularly, the poly(dialkylaminoalkyl (meth) acrylamide) used as an SAP, or as a component of an SAP, is lightly crosslinked and, in preferred embodiments, is surface treated to improve absorption and retention properties.

Accordingly, one aspect of the present invention is to provide an improved method of manufacturing an N-(dialkylaminoalkyl) (meth)acrylamide monomer that is used to prepare a poly(dialkylaminoalkyl (meth) acrylamide). The present method substantially increases the percent yield and purity of the N-(dialkylaminoalkyl) (meth) acrylamide monomer, and, therefore, provides a commercially useful process for manufacturing an N-(dialkylaminoalkyl) (meth)acrylamide monomer. Consequently, the improved method of preparing the monomer reduces process time and production costs.

Another aspect of the present invention is to provide an SAP having absorption and retention properties comparable to a conventional SAP, like sodium polyacrylate. A present SAP is produced by neutralizing a poly(dialkylaminoalkyl (meth)acrylamide), which can be crosslinked using a suitable polyfunctional vinyl monomer, with a sufficient amount of acid, like hydrochloric acid, such that at least about 10%, i.e., about 10% to 100%, of the aminefunctional groups are neutralized. The resulting poly(dialkylaminoalkyl (meth) acrylamide) salt is an excellent SAP for absorbing aqueous media.

In accordance with another important aspect of the present invention, a lightly crosslinked poly (dialkylaminoalkyl (meth)acrylamide), alone and unneutralized, can be used to absorb and retain acidic aqueous media, or to remediate acidic species. The acidic aqueous media converts a low-absorbing poly (dialkylaminoalkyl (meth)acrylamide) to a highly absorbing poly(dialkylaminoalkyl (meth)acrylamide) salt, i.e., converts the polymer to an SAP, during absorption. A poly (dialkylaminoalkyl (meth)acrylamide), therefore, is an excellent resin for cleaning acid spills.

Yet another aspect of the present invention is to provide an improved SAP that overcomes the salt poisoning effect of electrolytes. In particular, the improved SAP material contains a mixture of an acidic swellable resin, like polyacrylic acid, and a poly(dialkylaminoalkyl (meth)acrylamide).

In particular, one important aspect of the present invention is to provide an improved method of manufacturing an N-(dialkylaminoalkyl) (meth)acrylamide monomer having the general structural formula (I)

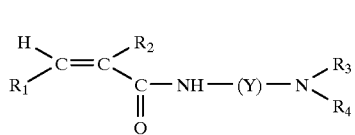

wherein $R_1$ and $R_2$, independently, are selected from the group consisting of hydrogen and methyl, Y is a divalent straight chain or branched organic radical, preferably alkyl, having 1 to 8 carbon atoms, and $R_3$ and $R_4$, independently, are alkyl radicals having 1 to 4 carbon atoms.

Another aspect of the present invention is to provide crosslinked polymers prepared from monomers of formula (I) that perform as SAPs. Yet another aspect of the present invention to surface treat the crosslinked polymers with a surface crosslinker to improve the absorption and retention properties of the poly(dialkylaminoalkyl (meth)acrylamide).

Another important aspect of the present invention is to provide crosslinked polymers from the ester analog of a monomer of formula (I), i.e., a (meth) acrylic acid ester monomer of structural formula (II)

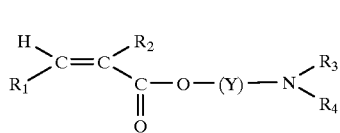

wherein Y, $R_1$, $R_2$, $R_3$, and $R_4$ are defined above, that perform as SAPs. Another aspect of the present invention is to surface crosslink a crosslinked polymer prepared from monomers of structural formula (II) to improve absorption and retention properties.

These and other aspects and advantages of the present invention will become apparent from the following detailed description of the preferred embodiments taken in conjunction with the drawings.

DETAILED DESCRIPTION OF THE PREFERRED EMBODIMENTS

Figure 1:
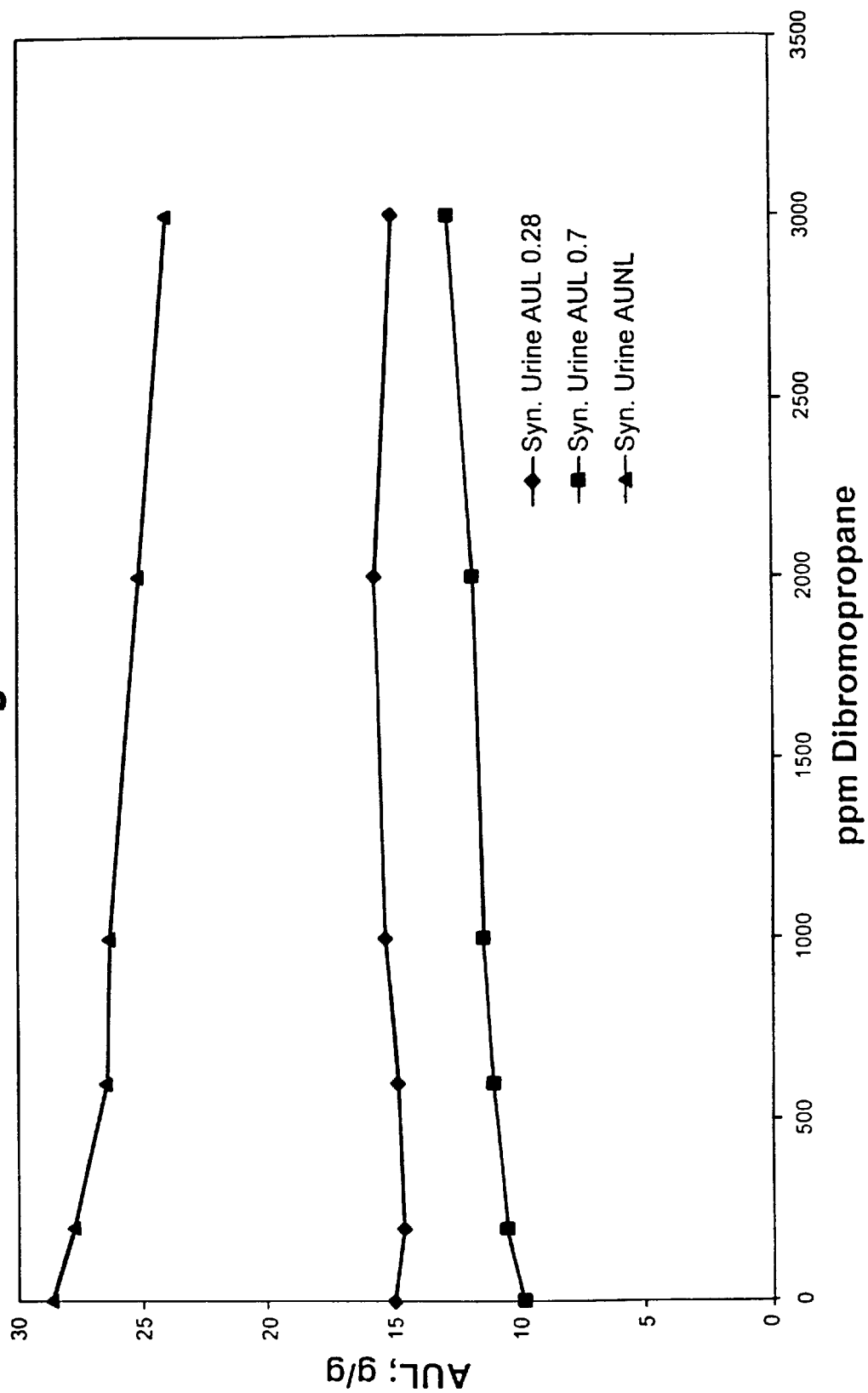
FIG. 1 contains plots of absorption of synthetic urine, in g/g, vs. ppm surface crosslinking for poly(DAEA) polymers crosslinked with dibromopropane.

The present invention is directed to: (a) an improved method of manufacturing N-(dialkylaminoalkyl) (meth) acrylamide monomers, (b) poly(dialkylaminoalkyl (meth) acrylamides), and salts thereof, and their use as SAPS, and (c) an improved SAP material comprising an admixture of a poly(dialkylaminoalkyl (meth)acrylamide) and an acidic water-absorbing resin.

(a) An Improved Method of Manufacturing Poly (dialkylaminoalkyl (meth)acrylamide) Monomers Poly(dialkylaminoalkyl (meth)acrylamides), and salts derived therefrom, are known polymers. The poly (dialkylaminoalkyl (meth)acrylamides) are prepared from N-(dialkylaminoalkyl) (meth)acrylamides of general structural formula (I) by standard free radical polymerization techniques. Polymers are similarly prepared from the (meth) acrylic acid ester monomers of general structural formula (II). The production of poly(dialkylaminoalkyl (meth) acrylamides) would be facilitated, and production costs decreased, by an improved method of preparing commercial quantities of the N-(dialkylaminoalkyl) (meth)acrylamide monomers. Therefore, in accordance with an important feature of the present invention, an improved method of manufacturing N-(dialkylaminoalkyl) (meth)acrylamide monomers is disclosed. Examples of N-(dialkylaminoalkyl) (meth)acrylamides include, for example, N-(2-dimethylaminoethyl) acrylamide, i.e., DAEA illustrated as structural formula (III), and N-(3-dimethylaminopropyl) methacrylamide, i.e., DMAPMA illustrated as structural formula (IV).

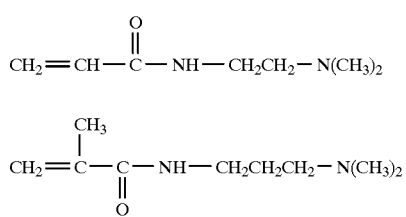

(III)

(IV)

The DMAPMA monomer is commercially available, but many N-(dialkylaminoalkyl) (meth)acrylamides, like DAEA, are not available commercially. As demonstrated hereafter, DAEA is a monomer that provides a useful water-absorbing hydrogel. However, no high yielding synthesis of DAEA from commercially available starting materials is known. In particular, the direct synthesis of DAEA from acryloyl chloride and N,N-dimethyl ethylenediamine typically suffers from low yields because of Michael additions to the active carbon-carbon double bond. Indirect synthetic routes to DAEA provide good yields, but the sequence requires several synthetic steps.

For example, Küster et al. U.S. Pat. No. 4,237,067 discloses a method of producing α,β-unsaturated N-substituted carboxamides by reacting a β-substituted carboxamide, and typically a β-hydroxy carboxamide, with an amine in a transamidation reaction, then driving off the β-substituent by using heat and a catalyst. The resulting α,β-unsaturated N-substituted carboxamides have a structure as set forth in structural formula (I). Y. Chang et al., *Macromolecules*, 26, pages 6121–6126 (1993) (Chang publication), discloses the preparation of N-(2-dimethylaminoethyl) acrylamide from N,N-dimethylethylenediamine and acryloyl chloride at 5° C.–10° C. The Chang publication discloses an aqueous workup to isolate the acrylamide. Attempts to repeat the method disclosed in the Chang publication resulted in low product yields.

The present method provides monomers of structural formula (I) in good yield and high purity from commercially available starting materials. In particular, the present method provides an N-(dialkylaminoalkyl) (meth)acrylamide having the structural formula:

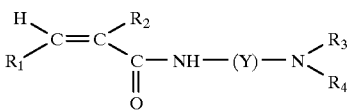

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms. The present method utilizes a simple synthetic scheme based on (meth)acryloyl chloride and a diamine having the structure

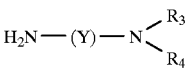

The diamine has a primary amine group and a tertiary amine group. The Y radical preferably is an alkyl moiety.

In general, the N-(dialkylaminoalkyl) (meth)acrylamide monomer is prepared by the following reaction sequence:

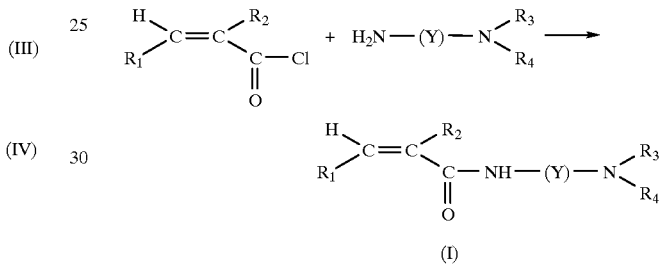

(I)

The Y radical of (meth)acrylamide (I) is straight chain or branched, and can be substituted, for example, with an aryl group, like phenyl. The Y radical also can be cyclic, for example, a cycloalkyl group or an aryl group, like phenyl. The cyclic Y radical can be unsubstituted or substituted.

Preferably, the Y radical is an alkyl radical, straight chain or branched, containing 2 to 5 carbon atoms. To achieve the full advantage of the present invention, the Y radical is an alkyl radical containing 2 to 4 carbon atoms.

The $R_3$ and $R_4$ radicals of (meth)acrylamide (I), independently, are selected from the group consisting of methyl, ethyl, propyl, isopropyl, n-butyl, sec-butyl, and t-butyl. $R_1$ and $R_2$, independently, are hydrogen or methyl.

In general, the present method of preparing an N-(dialkylaminoalkyl) (meth)acrylamide monomer reacts (meth)acryloyl chloride and the diamine at a temperature less than 10° C. initially, then at room temperature, followed by the addition of a base in a nonaqueous solvent. The base can be, for example, sodium hydroxide, potassium hydroxide, lithium hydroxide, tetramethylammonium hydroxide, or a basic ion exchange resin. The organic solvent can be an alcohol, like methanol, ethanol, or isopropyl alcohol, glycerol, dimethylsulfoxide, or hexamethylphosphoramide. A preferred base is sodium hydroxide and a preferred solvent is an alcohol, like methanol.

The preparation of N-(2-dimethylaminoethyl) acrylamide, i.e., DAEA, is illustrated in Example 1. It is important that the entire workup and isolation of the monomer is conducted under nonaqueous conditions. It has been found that eliminating the aqueous workup procedure disclosed in the Change publication substantially increases product yields.

EXAMPLE 1

Acryloyl chloride (187 grams, 2.1 mole) was dissolved in 1,000 ml (milliliters) of methylene chloride ($CH_2Cl_2$), under an argon atmosphere. The resulting solution was cooled to below 10° C., then a solution of N,N-dimethylethylenediamine (176 grams, 2 mole) in 200 ml of methylene chloride was slowly added to the acryloyl chloride solution. Cooling was maintained, and the addition rate was sufficiently slow to maintain the reaction temperature below 10° C. After addition of the diamine was complete, the resulting reaction mixture was allowed to warm to room temperature, then stirring was continued for about one hour. Next, a solution containing 10% (by weight) sodium hydroxide in methanol (800 g) was added to the reaction mixture, and the resulting mixture was stirred for one hour. The mixture then was filtered to remove the precipitated sodium chloride. The methanol and methylene chloride then were removed from the filtrate using a rotary evaporator. The resulting oil was vacuum distilled at 61° C. and 0.1 mm Hg. The distillate was collected in three fractions, each of which contained N-(2-dimethylaminoethyl) acrylamide of excellent purity. The distillation results are summarized below:

| Fraction | Mass (g) | Purity (% by GC) |
|---|---|---|
| 1 | 14 | 94 |
| 2 | 120 | 97 |
| 3 | 60 | 94 |

Overall yield of distilled acrylamide product was 68%.

The present method achieves excellent yields of the N-(dialkylaminoalkyl) (meth)acrylamide. However, it also has been found that the mole ratio of (meth)acryloyl chloride to diamine has an effect on the percent yield of N-(dialkylaminoalkyl) (meth)acrylamide monomer. In particular, the mole ratio of (meth)acryloyl chloride to diamine is maintained in a range of about 1.0:0.9 to about 1.0:1.1, and preferably about 1.0:0.95 to about 1.0:1.05.

To illustrate the effect of the mole ratio of (meth)acryloyl chloride to diamine on the percent yield of N-(dialkylaminoalkyl) (meth)acrylamide, the following Table 1 summarizes eight separate synthesis of DAEA.

TABLE 1

| Run | Moles Acryloyl Chloride | Moles Dimethyl-ethylenediamine | Yield (%) |
|---|---|---|---|
| 1 | 2.07 | 2.13 | 65 |
| 2 | 2.07 | 2.07 | 59 |
| 3 | 2.07 | 2.07 | 46 |
| 4 | 2.07 | 2.01 | 68 |
| 5 | 2.07 | 2.01 | 73 |
| 6 | 2.07 | 2.01 | 76 |
| 7 | 2.07 | 2.01 | 77 |
| 8 | 2.07 | 2.01 | 74 |

It was observed that yields were maximized at a mole ratio of (meth)acryloyl chloride to diamine of about 1.0 to about 0.97, as set forth in runs 4–8.

In accordance with an important feature of the present method of synthesizing an N-(dialkylaminoalkyl) (meth)acrylamide, the entire synthesis and work-up is performed in the absence of water. The Chang publication discloses the synthesis of DAEA from acryloyl chloride and dimethyl ethylenediamine, but the reaction mixture was washed with water twice and with concentrated sodium chloride once. Repeating the method disclosed in the Chang publication gave about a 10%–20% yield of DAEA. The present method, which omits the aqueous washes, and maintains a nonaqueous reaction mixture, achieves a percent yield of at least 50%, and in excess of about 75%. The present method, therefore, is an improved method of manufacturing an N-(dialkylaminoalkyl) (meth)acrylamide.

An N-(dialkylaminoalkyl) (meth)acrylamide, prepared either by the above-disclosed improved method or by a prior method, can be polymerized to form homopolymers or copolymers. In general, an uncrosslinked poly (dialkylaminoalkyl (meth)acrylamide) typically is a water-soluble polymer that has many practical applications, such as in water treatment, personal care products, and ion exchange resins. A poly(dialkylaminoalkyl (meth) acrylamide) is rendered water insoluble by crosslinking the polymer. Although poly(dialkylaminoalkyl (meth) acrylamides) and salts thereof, are well known, the use of such polymers as an SAP is relatively uninvestigated.

Typically, a poly(dialkylaminoalkyl (meth)acrylamide) polymer is produced by standard free radical polymerization techniques. For use in an SAP, it is preferred that the Y radical of the compound of structural formula (I) contains two to four carbon atoms, and that the $R_3$ and $R_4$ moieties contain one or two carbon atoms. Such N-(dialkylaminoalkyl) (meth)acrylamide monomers provide polymers having a sufficient hydrophilicity to perform as an excellent SAP. As the carbon chains of the Y, $R_3$, and $R_4$ radicals increase in number of carbon atoms, the hydrophilicity of the polymer decreases, and absorption and retention properties also may decrease.

It should be noted the poly(dialkylaminoalkyl (meth) acrylamide) polymer can contain other copolymerizable units, i.e., other monoethylenically unsaturated comonomers, as long as the polymer is substantially, i.e., at least 10%, and preferably at least 25%, poly (dialkylaminoalkyl (meth)acrylamide) units. To achieve the full advantages of the present invention, the poly (dialkylaminoalkyl (meth)acrylamide) contains at least 50%, and more preferably, at least 75%, N-(dialkylaminoalkyl) (meth)acrylamide units. The other copolymerizable units can, for example, help improve the hydrophilicity of the polymer.

As set forth above, polymerization of N-(dialkylaminoalkyl) (meth)acrylamide monomers is most commonly performed by free radical processes, either in the presence or absence of a crosslinker, i.e., a polyfunctional organic compound. In accordance with the present invention, a poly(dialkylaminoalkyl (meth)acrylamide) useful as an SAP is crosslinked. The uncrosslinked polymers are water soluble. SAPs, therefore, are crosslinked to a sufficient extent such that the polymer is water insoluble. Crosslinking renders the poly(dialkylaminoalkyl (meth)acrylamide) polymers substantially water insoluble, and, in part, serves to determine the absorption capacity of the polymers. For use in absorption applications, a poly(dialkylaminoalkyl (meth) acrylamide) is lightly crosslinked, i.e., has a crosslinking density of less than about 20%, and preferably less than about 10%, and most preferably about 0.01% to about 7%.

A crosslinking agent is used in an amount of less than about 7 wt %, and typically about 0.1 wt % to about 5 wt %, based on the total weight of monomers. A poly (dialkylaminoalkyl (meth)acrylamide) can be crosslinked by two different pathways. One pathway utilizes olefinically unsaturated crosslinking monomers that copolymerize with the N-(dialkylaminoalkyl) (meth)acrylamide, and, therefore, form a part of the polymeric backbone.

Examples of crosslinking polyvinyl monomers include, but are not limited to, polyacrylic (or polymethacrylic) acid esters represented by the following formula (V), and bisacrylamides, represented by the following formula (VI):

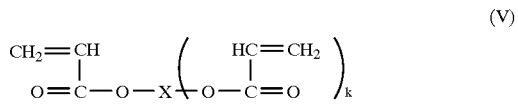

(V)

wherein x is ethylene, propylene, trimethylene, hexamethylene, 2-hydroxypropylene, —$(CH_2CH_2O)_n CH_2CH_2$—, or

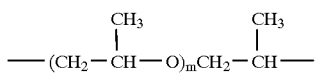

n and m are each an integer 5 to 40, and k is 1 or 2;

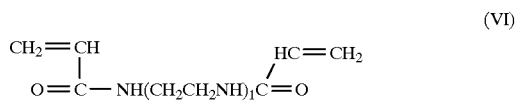

(VI)

wherein l is 2 or 3.

The compounds of formula (V) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (VI) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl) isocyanurate triacrylate, tris (2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, or mixtures thereof. Compounds like divinylbenzene and divinyl ether also can be used to crosslink the poly(dialkylaminoalkyl (meth)acrylamides). Especially preferred crosslinking agents are N,N'-methylenebisacrylamide, N,N'-methylenebismethacrylamide, ethylene glycol dimethacrylate, and trimethylolpropane triacrylate.

The following examples illustrate the preparation of crosslinked poly(dialkylaminoalkyl (meth)acrylamides).

EXAMPLE 2

Preparation of Poly(dimethylaminoethyl acrylamide) (Poly (DAEA))

A monomer mixture containing 125 grams N-(2-dimethylaminoethyl) acrylamide (DAEA), 300 grams deionized water, 0.6 gram methylenebisacrylamide, and 0.11 grams V-50 initiator (i.e., 2,2'-azobis(2-amidinopropane) hydrochloride initiator available from Wako Pure Chemical Industries, Inc., Osaka, Japan) was sparged with argon for 15 minutes. Then the resulting reaction mixture was placed in a shallow dish and polymerized under 15 mW/cm$^2$ of UV light for 25 minutes. The polymerization was exothermic, eventually reaching about 100° C. The resulting poly (DAEA) was a rubbery gel. The rubbery poly(DAEA) gel was crumbled by hand, then dried at 60° C. for 16 hours, and finally ground and sized through sieves to obtain the desired particle size.

EXAMPLE 3

Preparation of Poly(dimethylaminopropyl methacrylamide) Poly(DMAPMA)

A monomer mixture containing DMAPMA monomer (100 grams), deionized water (150 grams), methylenebisacrylamide (0.76 grams) and V-50 initiator (0.72 grams) was placed in a glass beaker. The monomer mixture was purged with argon for 25 minutes, covered, and then placed in an oven at about 60° C. for about 60 hours. The resulting poly(DMAPMA) was a rubbery gel. The rubbery poly (DMAPMA) gel was crumbled by hand, dried at 60° C. for 16 hours, and then ground and sized through sieves to obtain the desired particle size.

A poly (dialkylaminoalkyl (meth) acrylamide) also can be crosslinked in solution by suspending or dissolving an uncrosslinked poly(dialkylaminoalkyl (meth)acrylamide) in an aqueous or alcoholic medium, then adding a di- or poly-functional compound capable of crosslinking the poly (dialkylaminoalkyl (meth)acrylamide) by reaction with the amino groups of the polymer. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., WS $(O_2)O$—$(CH_2)_n$—$OS(O_2)W$, wherein n is 1 to 10 and W is methyl or tosyl), multifunctional epoxies (e.g., ethylene glycol diglycidyl ether), multifunctional carboxylic acids (e.g., succinic acid), melamine resins (e.g., CYMEL 301, CYMEL 303, CYMEL 370, and CYMEL 373 from Cytec Industries, Wayne, N.J.), and hydroxymethyl ureas (e.g., N,N'-dihydroxymethyl-4,5-dihydroxyethyleneurea).

In general, the crosslinking agent should be soluble in water or alcohol, and possess sufficient reactivity with the poly(dialkylaminoalkyl (meth)acrylamide) such that crosslinking occurs in a controlled fashion, preferably at a temperature of about 25° C. to about 150° C. A preferred crosslinking agent is, an alcohol-soluble dihaloalkane, and most preferably a dibromoalkane, and most preferably a dibromoalkane.

The following example illustrates light crosslinking of a poly(dialkylaminoalkyl (meth)acrylamide) using a polyfunctional crosslinking agent that reacts with the amino groups of the polymer.

EXAMPLE 4

To 2 liters of a 20% by weight isopropyl alcohol solution of uncrosslinked poly(DAEA) is added 10 g of dibromopropane. The resulting mixture is stirred, then the mixture is heated to about 70° C. and held for 16 hours to gel. The resulting gel then is extruded and dried to a constant weight at 80° C. The dried, lightly crosslinked poly(DAEA) then is milled to form a granular material capable of absorbing water or acid solutions.

In a preferred embodiment, a lightly crosslinked poly(dialkylaminoalkyl (meth)acrylamide) is subjected to a process step wherein the surface of the poly(dialkylaminoalkyl (meth)acrylamide) is further crosslinked. It has been found that surface crosslinking of a poly(dialkylaminoalkyl (meth) acrylamide) enhances the ability of the polymer to absorb and retain aqueous media under a load.

Surface crosslinking is achieved by spraying poly(dialkylaminoalkyl (meth)acrylamide) particles with a solution of a surface crosslinking agent to wet predominantly only the outer surfaces of the poly(dialkylaminoalkyl (meth)acrylamide) particles. Surface crosslinking and drying of the polymer then is performed, preferably by heating at least the wetted surfaces of the poly(dialkylaminoalkyl (meth)acrylamide) particles.

Typically, the poly(dialkylaminoalkyl acrylamide) particles are surface treated with an alcoholic solution of a surface crosslinking agent. The particles can be in the form of granules, a foam, beads, fibers, flakes, or powders, for example. The solution contains about 0.01% to about 4%, by weight, surface crosslinking agent, and preferably about 0.4% to about 2%, by weight, surface crosslinking agent in a suitable solvent. The solution can be applied as a fine spray onto the surface of freely tumbling poly(dialkylaminoalkyl (meth)acrylamide) particles at a ratio of about 1:0.01 to about 1:0.5 parts by weight poly(dialkylaminoalkyl (meth)acrylamide) to solution of surface crosslinking agent. The surface crosslinker is present in an amount of 0% to about 1%, by weight of the poly(dialkylaminoalkyl (meth)acrylamide), and preferably 0% to about 0.5% by weight. To achieve the full advantage of the present invention, the surface crosslinker is present in an amount of about 0.001% to about 0.1% by weight.

The crosslinking reaction and drying of the surface-treated poly(dialkylaminoalkyl (meth)acrylamide) particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the poly(dialkylaminoalkyl (meth)acrylamide) particle, and any other method of drying the poly(dialkylaminoalkyl (meth)acrylamide) particles, such as microwave energy, or the like, can be used.

Suitable surface crosslinking agents include di- or polyfunctional molecules capable of reacting with amino groups and crosslinking a poly(dialkylaminoalkyl (meth)acrylamide). Preferably, the surface crosslinking agent is alcohol or water soluble and possesses sufficient reactivity with a poly(dialkylaminoalkyl (meth)acrylamide) such that crosslinking occurs in a controlled fashion at a temperature of about 25° C. to about 150° C.

Nonlimiting examples of suitable surface crosslinking agents include:

(a) dihalides, for example, compounds of the formula

wherein p is a number from 2 to 12, and Z, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, like epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids, for example, di- and poly-carboxylic acids containing two to twelve carbon atoms, like oxalic acid, adipic acid, succinic acid, dodecanoic acid, malonic acid, and glutaric acid;

(g) melamine resins, like the CYMEL resins available from Cytec Industries, Wayne, N.J.; and (h) hydroxymethyl ureas, like N,N'-dihydroxymethyl-4,5-dihydroxyethylene urea.

A preferred surface crosslinking agent is a dihaloalkane which crosslinks a poly(dialkylaminoalkyl (meth)acrylamide) at a temperature of about 25° C. to about 150° C. Especially preferred surface crosslinking agents are dibromoalkanes containing 3 to 10 carbon atoms.

The following Example 5 illustrates surface treatment and crosslinking of a lightly crosslinked poly(dialkylaminoalkyl (meth)acrylamide).

EXAMPLE 5

Surface Crosslinked Poly(DAEA)

Individual portions of the lightly crosslinked poly(DAEA) of Example 2 were surface treated with dibromopropane at different levels (i.e., 0 to 3,000 ppm), then dried at about 105° C. to provide a surface crosslink. The surface crosslinked poly(DAEA) polymers then were tested, individually, for an ability to absorb and retain 0.1 M hydrochloric acid.

In the test results set forth below, the surface crosslinked polymers were tested for absorption under no load (AUNL) and absorption under load at 0.28 psi and 0.7 psi (AUL (0.28 psi) and AUL (0.7 psi)). Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g +/-0.001 g) is carefully scattered onto a 140-micron, water-permeable mesh attached to the base of a hollow plexiglass cylinder with an internal diameter of 25 mm. The sample is covered with a 100 g cover plate and the cylinder assembly weighed. This gives an applied pressure of 20 g/cm$^2$ (0.28 psi). Alternatively, the sample can be covered with a 250 g cover plate to give an applied pressure of 51 g/cm$^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact. As discussed hereafter, the poly(dialkylaminoalkyl (meth)acrylamide) particles also can be surface treated with a surface crosslinking agent, like dibromooctane, to give an absorbent having improved performance under external pressure.

Figure 2:
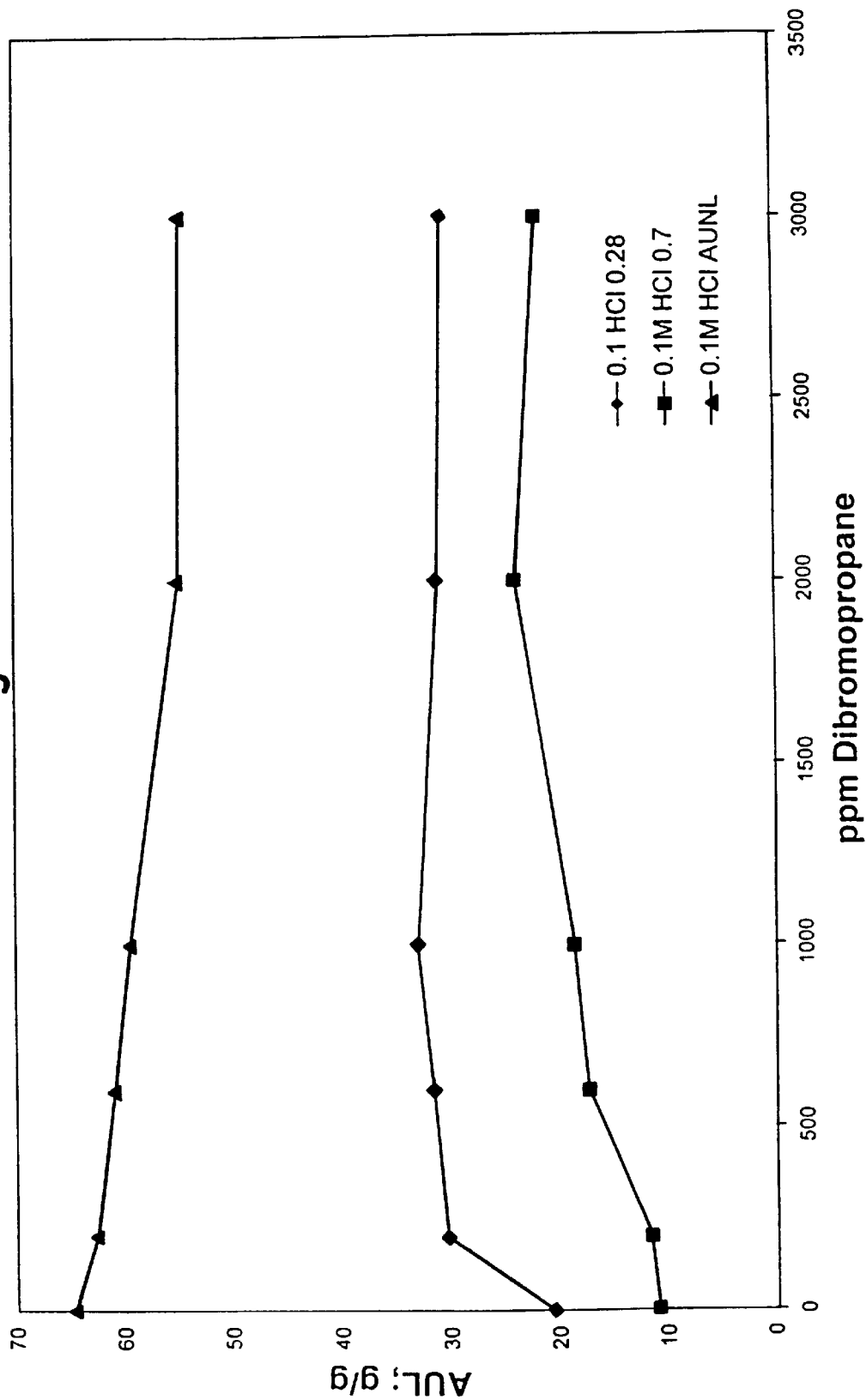
FIG. 2 contains plots of absorption, in g/g, of 0.1 M hydrochloric acid vs. ppm surface crosslinking for poly (DAEA) polymers crosslinked with dibromopropane.

The ability of a surface crosslinked poly(DAEA) to absorb and retain synthetic urine and 0.1 M hydrochloric acid is illustrated in FIGS. 1 and 2, respectively. FIGS. 1 and 2 show AUNL and AUL, at 0.28 psi and 0.7 psi, for poly(DAEA) polymers surface crosslinked with 0 to 10,000 ppm dibromopropane. As explained in detail hereafter, FIGS. 1 and 2 show that a poly(dialkylaminoalkyl (meth)acrylamide) has an excellent ability to absorb and retain acidic media (compare FIG. 2 to FIG. 1) and that surface crosslinking improves the AUL of a poly(dialkylaminoalkyl (meth)acrylamide).

Figure 3:
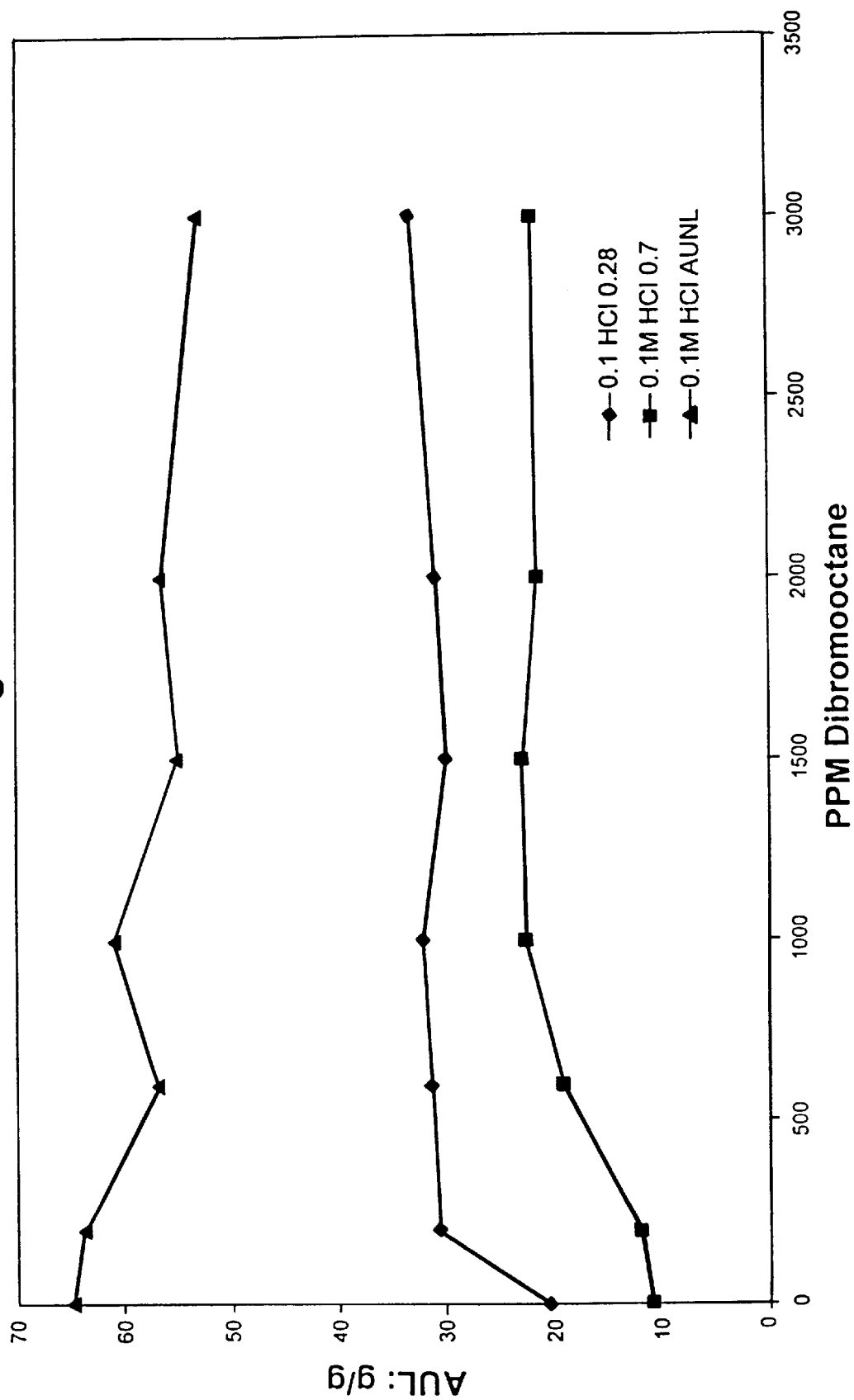
FIG. 3 contains plots of absorption, in g/g, of 0.1 M hydrochloric acid vs. ppm surface crosslinking for poly (DAEA) polymers crosslinked with dibromooctane.

Similar to the surface crosslinked poly(DAEA) polymers of Example 5, surface crosslinking of poly(DAEA) polymers with 0 to 10,000 ppm of 1,8-dibromooctane provided a surface crosslinked poly(DAEA) that had an excellent ability to absorb and retain acidic media, i.e., media having a pH less than 7, and further showed that surface crosslinking improved the AUL of a poly(dialkylaminoalkyl (meth) acrylamide). The results are illustrated in the plots of FIG. 3.

Poly(dialkylaminoalkyl (meth)acrylamide)-based SAPs

A poly (dialkylaminoalkyl (meth) acrylamide) typically does not function as an SAP in its neutral form because there is no ionic charge on the polymer. This is illustrated in FIG. 1 showing the relatively poor absorption and retention properties for a neutral poly(DAEA) absorbing synthetic urine. However, when converted to a salt, or used in conjunction with an acidic water-absorbing resin, like a polyacrylic acid, a poly(dialkylaminoalkyl (meth)acrylamide) then behaves like an SAP.

(i) Salts of a Poly(dialkylaminoalkyl (meth) acrylamide)

As previously discussed, sodium poly(acrylate) is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

A poly(dialkylaminoalkyl (meth)acrylamide) is a neutral polymer, and, accordingly, does not possess the polyelectrolytic properties necessary to provide an SAP. However, poly(dialkylaminoalkyl (meth)acrylamide) salts have polyelectrolytic properties sufficient to provide an SAP. The poly(dialkylaminoalkyl (meth)acrylamide) used to provide an SAP is a lightly crosslinked poly (dialkylaminoalkyl (meth) acrylamide), and preferably is surface crosslinked, as set forth above.

Such lightly crosslinked, and optionally surface crosslinked, poly(dialkylaminoalkyl (meth)acrylamide) polymers can be converted into salts by methods known in the art. For example, the preparation of a poly(vinylamine) salt by the addition of hydrochloric acid to a poly (vinylamine) is set forth in Pinschmidt, Jr. et al. U.S. Pat. No. 5,085,787, and in Gless, Jr. et al. U.S. Pat. No. 4,018,826. A similar method can be used to provide a salt of a poly (dialkylaminoalkyl (meth)acrylamide).

A poly(dialkylaminoalkyl (meth)acrylamide) salt useful as an SAP, however, is not limited to the hydrochloride salt. A poly(dialkylaminoalkyl (meth)acrylamide) can be reacted with a variety of acids to provide a poly(dialkylaminoalkyl (meth)acrylamide) salt useful as an SAP, but the preferred acids are mineral acids. To achieve the full advantage of the present invention, the poly(dialkylaminoalkyl (meth) acrylamide) salt is a hydrochloride salt.

To demonstrate the ability of a poly(dialkylaminoalkyl (meth)acrylamide) salt to act as an SAP, the lightly crosslinked poly(DAEA) of Example 2 was produced from a monomer that was partially neutralized with hydrochloric acid. The poly(DAEA) salt was tested for its ability to absorb and retain deionized water and electrolyte-containing aqueous media (i.e., up to 1% by weight aqueous sodium chloride).

In particular, DAEA monomer samples were converted to the hydrochloride salt using different amounts of 1N hydrochloric acid (HCl). The resulting solutions were polymerized as set forth in Example 2, and evaluated for an ability to absorb aqueous NaCl solutions. The results are summarized in Table 2.

TABLE 2

| Weight % NaCl | Mole % HCl | AUL (0.28 psi) | AUL (0.7 psi) |
|---|---|---|---|
| 0 | 0 | 14.2 | 7.7 |
|   | 50 | 30.8 | 14.6 |
|   | 100 | 23.2 | 14.6 |
| 0.5 | 0 | 16.7 | 8.9 |
|   | 50 | 18.8 | 10.8 |
|   | 100 | 14.1 | 11.8 |
| 1.0 | 0 | 12.2 | 8.9 |
|   | 50 | 16.6 | 11.8 |
|   | 100 | 13.2 | 10.9 |

The absorption and retention results summarized in Table 2 show that absorption increases dramatically, both under load and under no load, when the poly(DAEA) is converted to a hydrochloride salt. In accordance with an important feature of the present invention, a poly(dialkylaminoalkyl (meth)acrylamide) exhibits the properties of an SAP when converted to a salt in an amount of about 10 to about 100, and preferably about 20 to about 90, mole percent. To achieve the full advantage of the present invention, the poly(dialkylaminoalkyl (meth)acrylamide) is converted to a salt in an amount of about 25 to about 75 mole %, based on the weight of N-(dialkylaminoalkyl) (meth)acrylamide monomer used to prepare the poly(dialkylaminoalkyl (meth) acrylamide).

In another test, a lightly crosslinked poly(DAEA), as prepared in Example 2, was surface treated with various levels of dibromooctane in isopropyl alcohol, followed by drying and curing at 105° C. The surface crosslinked particles of lightly crosslinked poly(DAEA) then were partially neutralized (i.e., 75 mole %) with 1N HCl. The surface crosslinked poly(DAEA) salt, then was tested for an ability to absorb and retain a 0.9% aqueous NaCl solution. The results are summarized in Table 3, and show that a neutralized and surface crosslinked poly(DAEA) has an improved AUL.

TABLE 3

| Surface Crosslink Level (ppm) | AUNL | AUL (0.28 psi) | AUL (0.7 psi) |
|---|---|---|---|
| 0 | 30.2 | 17.9 | 10.4 |
| 500 | 28.1 | 20.9 | 15.5 |
| 1500 | 31.0 | 19.4 | 15.2 |
| 3000 | 27.3 | 19.6 | 15.6 |

(ii) A Poly(dialkylaminoalkyl (meth)acrylamide) in SAPs

As illustrated above and in FIG. 1, a poly (dialkylaminoalkyl (meth)acrylamide), in its free base form, does not function as an SAP for neutral-to-basic aqueous media. Similarly, polyacrylic acid, in its free acid form, does not function as an SAP for neutral-to-acidic aqueous media. In each case, the polymer has a low charge density, and, accordingly, a major driving force for absorption and retention, i.e., electrostatic repulsion, is missing. In contrast, partially neutralized polyacrylic has a sufficient charge density, and is currently used as an SAP by itself. Similarly, as disclosed above, poly(dialkylaminoalkyl (meth) acrylamide) salts have a high charge density and are excellent SAPs.

However, a poly(dialkylaminoalkyl (meth)acrylamide), in its free base form, can act as an absorbent for acidic aqueous media, as illustrated in FIGS. 2 and 3, wherein one gram of poly(DAEA) absorbed greater than 50, and up to about 65 g, of 0.1 M hydrochloric acid under no load and under load. The acidic media protonates the tertiary amino groups of the poly(dialkylaminoalkyl (meth)acrylamide), thereby providing sufficient charge density for the protonated poly (dialkylaminoalkyl (meth)acrylamide) to perform as an SAP. Accordingly, a poly(dialkylaminoalkyl (meth)acrylamide), by itself, can be used to absorb acidic aqueous media, for example, to absorb an acid spill.

It also has been found that poly(dialkylaminoalkyl (meth) acrylamide) polymers, in their free base form, are useful components in superabsorbent materials further containing an acidic water-absorbing resin. For example, a superabsorbent material of the present invention is an admixture of a poly(dialkylaminoalkyl (meth)acrylamide) and an acidic water-absorbing resin, like polyacrylic acid. The present superabsorbent materials are particularly useful with respect to absorbing and retaining aqueous media containing electrolytes.

Currently, superabsorbent materials containing two absorbing components, i.e., bi-component SAP materials, are being investigated as an improved class of SAPs. Typically, one component is a water-absorbing resin, and the second component acts in an ion exchange capacity to remove electrolytes from an aqueous media.

In contrast, the present invention is directed to a bi-component SAP material comprising two uncharged, slightly crosslinked polymers, each of which is capable of swelling and absorbing aqueous media. When contacted with water or an aqueous electrolyte-containing medium, the two uncharged polymers neutralize each other to form a superabsorbent material. Neither polymer in its uncharged form behaves as an SAP by itself when contacted with water. The present bi-component superabsorbent material, therefore, contains two resins, one acidic and one basic, which are capable of acting as an absorbent material in their polyelectrolyte form. While polyacrylic acid is an excellent choice for the acidic resin, until the present invention, there has not been an adequate basic resin.

Therefore, in accordance with an important feature of the present invention, a poly(dialkylaminoalkyl (meth) acrylamide) is used as the basic resin for a bi-component SAP material. The poly(dialkylaminoalkyl (meth) acrylamide) is lightly crosslinked, and the poly (dialkylaminoalkyl (meth)acrylamide) particles preferably are surface crosslinked to improve absorption and retention properties. The poly(dialkylaminoalkyl (meth)acrylamide) and acidic resin combination behaves like an SAP in the presence of water, and especially brackish water. The poly (dialkylaminoalkyl (meth)acrylamide) can be prepared by methods known in the art. Crosslinking and surface crosslinking can be performed as set forth above.

The poly (dialkylaminoalkyl (meth) acrylamide) is a basic resin that is admixed with an acidic resin. The acidic resin can be any resin that acts as an SAP in its neutralized form. The acidic resin typically contains a plurality of carboxylic acid, sulfonic acid, phosphonic acid, phosphoric acid, or sulfuric acid moieties, or a mixture thereof.

Examples of acidic resins include, but are not limited to, polyacrylic acid, hydrolyzed starchacrylonitrile graft copolymers, starch-acrylic acid graft copolymers, saponified vinyl acetate-acrylic ester copolymers, hydrolyzed acrylonitrile or acrylamidecopolymers, ethylene-maleic anhydride copolymers, isobutylene-maleic anhydride copolymers, poly(vinylsulfonic acid), poly(vinylsulfuric acid), poly (vinylphosphonic acid), poly(vinylphosphoric acid), sulfonated polystyrene, and mixtures thereof. The preferred acidic resins are the polyacrylic acids.

The poly (dialkylaminoalkyl (meth)acrylamide) is present in its free base, i.e., amine, form, and the acidic resin is present in its free acid form. It is envisioned that a low percentage, i.e., about 25% or less, of the amine and/or acid functionalities can be in their charged form. The low percentage of charged functionalities does not adversely affect performance of the superabsorbent material, and can assist in the initial absorption of a liquid.

The poly (dialkylaminoalkyl (meth)acrylamide) and acidic resin are admixed in a weight ratio of about 10:90 to about 90:10, and preferably about 20:80 to about 80:20. To achieve the full advantage of the present invention, the resins are admixed in a weight ratio of about 25:75 to about 75:25. A present bi-component SAP material is prepared by simply admixing particles of the poly(dialkylaminoalkyl (meth)acrylamide) and acidic resin to provide a uniform particulate material.

To illustrate a present bi-component SAP material, the following examples were prepared and tests performed.

EXAMPLE 6

A series of mixtures containing powdered poly(DAEA), as prepared in Example 2 (particle size 210–710 $\mu$m), and lightly crosslinked polyacrylic acid (particle size 210–710 $\mu$m) were prepared in weight ratio of poly(DAEA) to polyacrylic acid over the range of 0:100 to 100:0. The absorption and retention properties of the resulting bi-component SAP blends were tested under load and no load, and the results are illustrated in FIG. 4.

Figure 4:
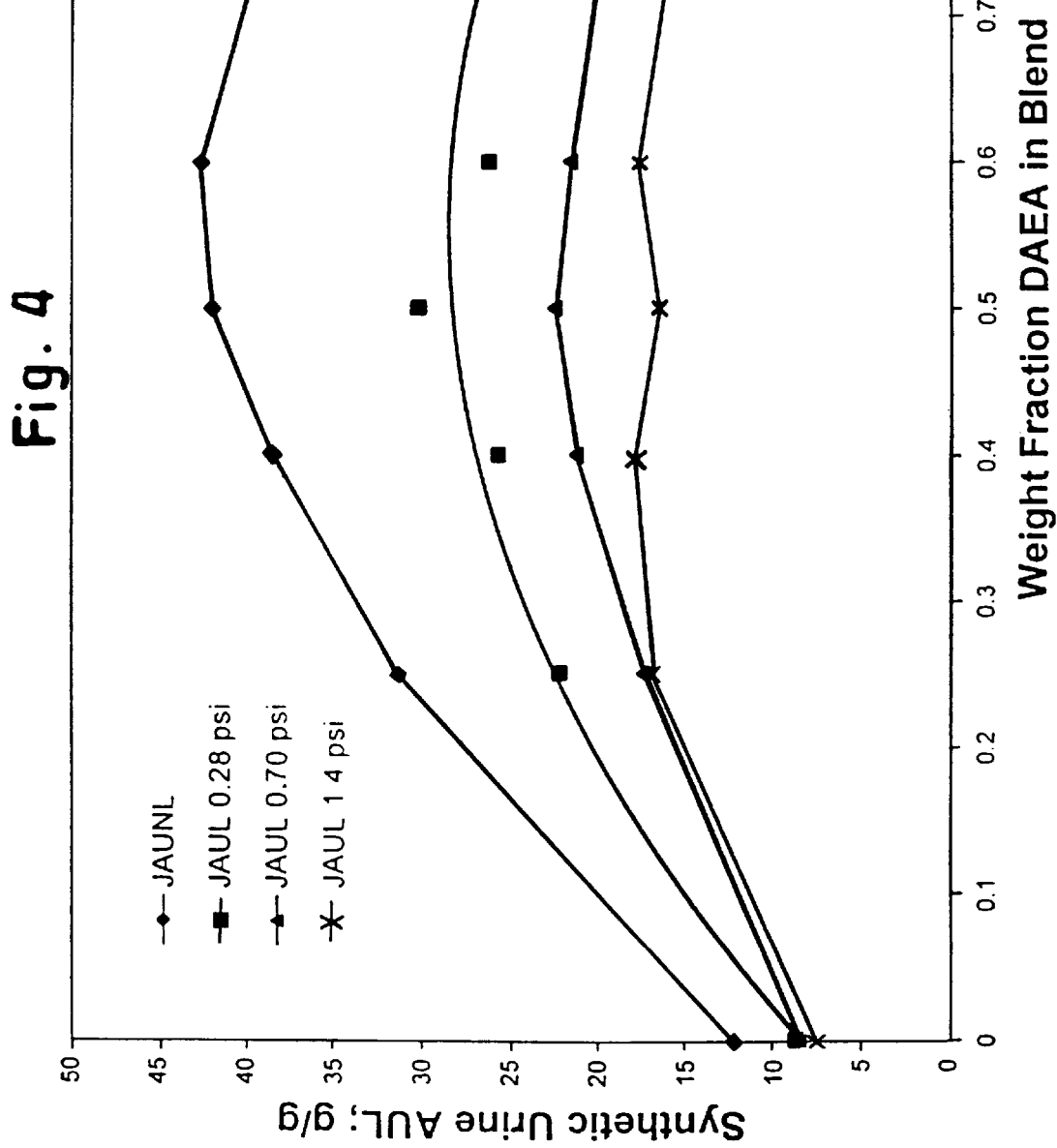
FIG. 4 contains plots of absorption, in g/g, of synthetic urine by blends of poly(DAEA) and polyacrylic acid.

The plots of FIG. 4 show that a poly(DAEA) and a polyacrylic acid, alone, each have a relatively poor ability to perform as an SAP, i.e., absorption of synthetic urine ranges from less than 10 to about 25 grams per gram of resin. However, a blend of poly(DAEA) and polyacrylic acid substantially increases absorption and retention, both AUNL and AUL, especially at a weight fraction range of poly (DAEA) in the blend of about 0.1 to about 0.9.

Figure 5:
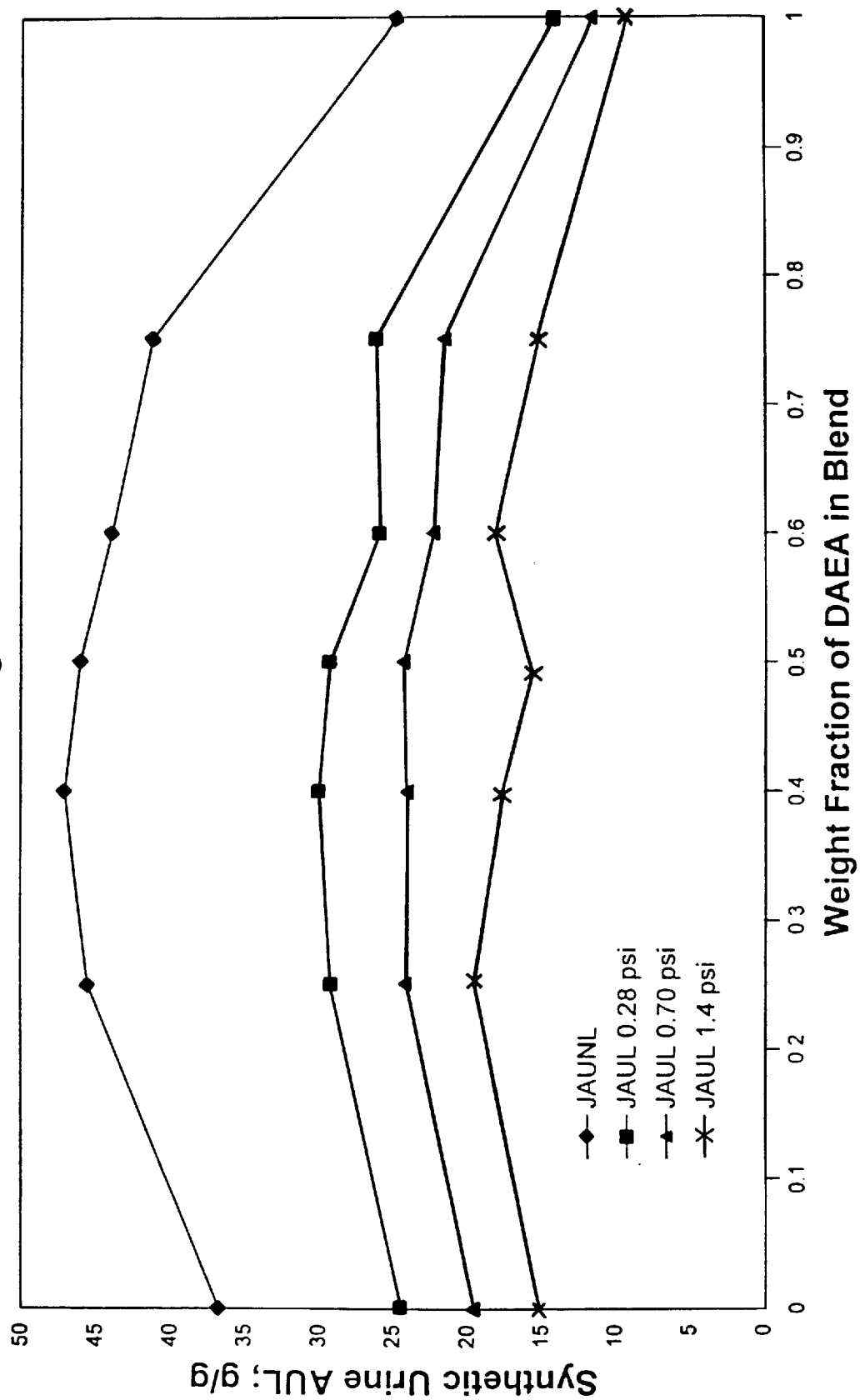
FIG. 5 contains plots of absorption, in g/g, of synthetic urine by blends of poly(DAEA) and 20% neutralized polyacrylic acid.
Figure 6:
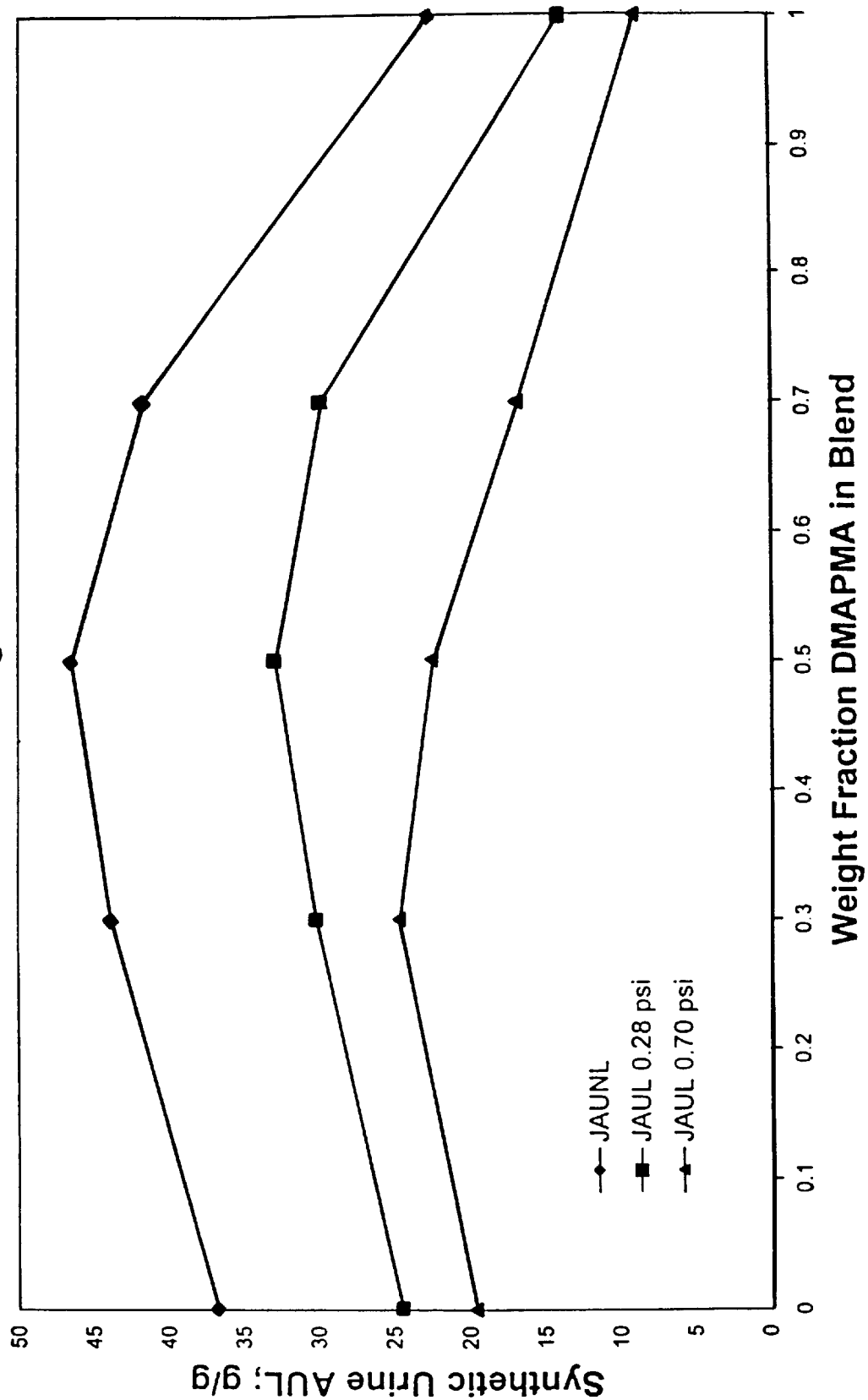
FIG. 6 contains plots of absorption, in g/g, of synthetic urine by blends of poly(DMAPMA) and 20% neutralized polyacrylic acid.

Example 6 was repeated using blends of poly(DAEA) and a 20% neutralized polyacrylic acid. The results of this test are summarized in the plots of FIG. 5, which show that blends containing a poly(dialkylaminoalkyl) (meth) acrylamide) and an acid-containing polymer substantially improve the absorption and retention properties of the individual resins. FIG. 6 shows similar results for blends of poly(DMAPMA) and a 20% neutralized polyacrylic acid.

The bi-component SAP materials are especially useful in articles designed to absorb and retain liquids, especially electrolyte-containing liquids. Such articles include, for example, diapers and catamenial devices.

The following tables further illustrate the improved ability of a bi-component SAP to absorb and retain a 0.9% saline solution compared to either individual component of the bi-component SAP.

TABLE 4

Poly(DAEA), Polyacrylic Acid, and Bi-component SAP of Poly(DAEA) and Polyacrylic Acid

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DAEA)[1)] alone | 9.6 | 8.1 | 23.9 | 13.5 | 9.3 | 24.2 |
| Polyacrylic Acid[2)] alone | 11.9 | 10.8 | 14.3 | 12.0 | 10.8 | 14.3 |
| Bi-component SAP-1[3)] | 11.0 | 10.9 | 45.2 | 14.8 | 14.4 | 48.0 |
| Bi-component SAP-2[4)] | 12.5 | 9.6 | 26.7 | 18.9 | 13.1 | 30.1 |
| Bi-component SAP-3[5)] | 12.4 | 11.3 | 37.3 | 16.5 | 14.7 | 42.3 |
| Bi-component SAP-4[6)] | 20.1 | 17.2 | 28.6 | 24.7 | 20.7 | 34.1 |
| Bi-component SAP-5[7)] | 25.3 | 18.2 | 35.3 | 28.1 | 23 | 38.7 |

[1)]particle size - 180–710 #m;
[2)]0% neutralization, particle size - 180–710 μm, surface crosslinked - 600 ppm EGDGE;
[3)]60% poly(DAEA), particle sizes less than 180 nm, 40% polyacrylic acid - 0% neutralized;
[4)]60% poly(DAEA), particle sizes less than 180 nm, 40% polyacrylic acid - 0% neutratized, crosslinked with 600 ppm EGDGE;
[5)]60% poly(DAEA), particle size - 180–710 μm, 40% polyacrylic acid - 0% neutralized;
[6)]60% poly(DAEA), particle size - 180–710 μm, 40% polyacrylic acid - 0% neutralized, crosslinked with 600 ppm EGDGE; and
[7)]60% poly(DAEA), particle sizes less than 180 μm, 40% polyacrylic acid - 20% neutralized, particle size 180–710 μm.

TABLE 5

Poly(DMAPMA), Polyacrylic Acid, and Bi-component SAP of Poly(DMAPMA) and Polyacrylic Acid

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DMAPMA)[8)] alone | 10.2 | 8.6 | 18 | 11.4 | 10 | 18.3 |
| Poly(DMAPMA)[9)] alone | 9.3 | 5.2 | 17.4 | 11 | 6.9 | 17.8 |
| Polyacrylic acid[10)] | 11.9 | 10.8 | 14.3 | 12.0 | 10.8 | 14.3 |
| Bi-component SAP-6[11)] | 14.5 | 10.9 | 18.8 | 17.2 | 14.3 | 20.9 |
| Bi-component SAP-7[12)] | 14 | 12 | 38.7 | 17.9 | 15.7 | 43.6 |
| Bi-component SAP-8[13)] | 12.5 | 10.4 | 24.8 | 14.5 | 12.4 | 24.8 |

[8)]Poly(DMAPMA), particle size less than 106 μm;
[9)]Poly(DMAPMA), particle size 106–180 μm;
[10)]Polyacrylic acid, particle size 180–710 μm, 0% neutralized, surface crosslinked with 600 ppm EGDGE;
[11)]60% Poly(DMAPMA), particle size 106–180 μm, 40% polyacrylic acid - 0% neutralized;
[12)]60% Poly(DMAPMA), particle size <106 μm, 40% polyacrylic acid - 0% neutralized; and
[13)]50% Poly(DMAPMA), 50% polyacrylic acid - 0% neutralized.

Many modifications and variations of the invention as hereinbefore set forth can be made without departing from the spirit and scope thereof and, therefore, only such limitations should be imposed as are indicated by the appended claims.

What is claimed is:

1. A solid superabsorbent material comprising a mixture of
   (a) discrete particles of a lightly crosslinked poly (dialkylaminoalkyl (meth)acrylamide), and
   (b) discrete particles of an acidic water-absorbing resin.

2. The superabsorbent material of claim 1 wherein the poly(dialkylaminoalkyl (meth) acrylamide) is surface crosslinked.

3. The superabsorbent material of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly (vinylsulfonic acid), a poly(vinylsulfuric acid), a poly (vinylphosphonic acid), a poly(vinylphosphoric acid), a sulfonated polystyrene, and mixtures thereof.

4. The superabsorbent material of claim 1 wherein the poly(dialkylaminoalkyl (meth)acrylamide) and the acidic resin are present in a weight ratio of about 10:90 to about 90:10.

5. A method of absorbing an aqueous medium comprising contacting the medium with a superabsorbent material of claim 1.

6. A solid superabsorbent material comprising a mixture of
   (a) discrete particles of a lightly crosslinked polymer prepared from an acrylic acid ester monomer having the formula $$\underset{R_1}{\overset{H}{>}}C=C\underset{\underset{O}{\overset{\|}{C}-NH-(Y)-N}}{\overset{R_2}{<}}\underset{R_4}{\overset{R_3}{<}}$$

wherein $R_1$ and $R_2$, independently, are selected from the group consisting of hydrogen and methyl, Y is a divalent organic radical having 1 to 8 carbon atoms, and $R_3$ and $R_4$, independently, are alkyl radicals having 1 to 4 carbon atoms, and
   (b) discrete particles of an acidic water-absorbing resin.

7. The superabsorbent material of claim 6 wherein the acidic resin is selected from the group consisting of polyacrylic acid, a hydrolyzed starch-acrylonitrile graft copolymer a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphonic acid), a poly(vinylphosphoric acid), a sulfonated polystyrene, and mixtures thereof.

8. The superabsorbent material of claim 6 wherein the polymer and the acidic resin are present in a weight ratio of about 10:90 to about 90:10.

9. A method of absorbing an aqueous medium comprising contacting the medium with a superabsorbent material of claim 6.

10. A solid superabsorbent material comprising a mixture of
   (a) particles of a lightly crosslinked poly(diakylaminoalkyl (meth)acrylamide), and
   (b) particles of an acidic water-absorbing resin,
   wherein the poly(dialkylaminoalkyl (meth)acrylamide) is surface crosslinked using a surface crosslinking agent comprising a dihaloalkane containing 2 to 10 carbon atoms.

11. The superabsorbent material of claim 10 wherein the dihaloalkane comprises a dibromoalkane.

12. The superabsorbent material of claim 1 wherein the poly(dialkylaminoalkyl (meth)acrylamide) is lightly crosslinked with a polyvinyl monomer comprising

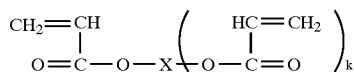

wherein x is ethylene, propylene, trimethylene, hexamethylene, 2-hydroxypropylene, —(CH$_2$CH$_2$O)$_n$CH$_2$CH$_2$—; or

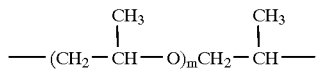

wherein n and m are an integer 5 to 40, and k is 1 or 2;

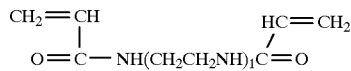

wherein 1 is 2 or 3; or a mixture thereof.

13. The superabsorbent material of claim 1 wherein the poly(dialkylaminoalkyl (meth)acrylamide) is lightly crosslinked with a polyvinyl monomer comprising divinylbenzene, divinyl ether, or a mixture thereof.

14. The superabsorbent material of claim 1 wherein the poly(dialkylaminoalkyl (meth)acrylamide) is lightly crosslinked with a polyfunctional compound selected from the group consisting of a multifunctional aldehyde, a multifunctional acrylate, a halohydrin, a multifunctional epoxy, a multifunctional carboxylic acid, a melamine resin, a hydroxymethyl urea, and mixtures thereof.

15. The superabsorbent material of claim 2 wherein the poly(dialkylaminoalkyl (meth)acrylamide) is surface crosslinked with up to about 10,000 ppm of a surface crosslinking agent.

16. The superabsorbent material of claim 2 wherein the poly(dialkylaminoalkyl (meth)acrylamide) is surface crosslinked with a surface crosslinking agent selected from the group consisting of (a) a dihalide having the formula

wherein p is an integer 2 to 12 and z, independently, is selected from the group consisting of halo, tosylate, mesylate, an alkyl sulfonate ester, and an aryl sulfonate ester;

(b) a multifunctional aziridine;

(c) a multifunctional aldehyde, and acetals and bisulfites thereof;

(d) a halohydrin;

(e) a multifunctional epoxy compound;

(f) a multifunctional carboxylic acid containing two to twelve carbon atoms;

(g) a melamine resin; and (h) a hydroxymethyl urea.

17. The superabsorbent material of claim 1 wherein the poly(dialkylaminoalkyl (meth)acrylamide) comprises poly(dimethylaminoethyl acrylamide).

18. The superabsorbent material of claim 1 wherein the poly(dialkylaminoalkyl (meth)acrylamide) comprises poly(dimethylaminopropyl methacrylamide).

19. The superabsorbent material of claim 6 wherein the lightly crosslinked acrylic acid-ester polymer is surface crosslinked.

* * * * *